(12) United States Patent
Lutz et al.

(10) Patent No.: US 10,398,482 B2
(45) Date of Patent: Sep. 3, 2019

(54) INTRAMEDULLARY NAIL

(71) Applicant: SWEMAC INNOVATION AB, Linköping (SE)

(72) Inventors: Christian Lutz, Heikendorf (DE); Klaus Dorawa, Schönkirchen (DE)

(73) Assignee: SWEMAC INNOVATION AB, Linkoping (SE)

( * ) Notice: Subject to any disclaimer, the term of this patent is extended or adjusted under 35 U.S.C. 154(b) by 62 days.

(21) Appl. No.: 15/526,764

(22) PCT Filed: Nov. 25, 2014

(86) PCT No.: PCT/EP2014/075489
§ 371 (c)(1),
(2) Date: May 15, 2017

(87) PCT Pub. No.: WO2016/082861
PCT Pub. Date: Jun. 2, 2016

(65) Prior Publication Data
US 2017/0333096 A1 Nov. 23, 2017

(51) Int. Cl.
A61B 17/72 (2006.01)
A61B 17/74 (2006.01)

(52) U.S. Cl.
CPC ........ *A61B 17/744* (2013.01); *A61B 17/7241* (2013.01)

(58) Field of Classification Search
CPC ... A61B 17/7241; A61B 17/744; A61B 17/72; A61B 17/7233
See application file for complete search history.

(56) References Cited

U.S. PATENT DOCUMENTS

| 5,549,610 A | 8/1996 | Russell et al. |
| 7,976,570 B2 * | 7/2011 | Wagner ............... A61B 17/8057 606/291 |
| 8,449,544 B2 * | 5/2013 | Grusin ............... A61B 17/7225 606/64 |

(Continued)

FOREIGN PATENT DOCUMENTS

| JP | 2011206420 | 10/2011 |
| WO | 2008147975 | 12/2008 |

(Continued)

*Primary Examiner* — Jacqueline T Johanas
(74) *Attorney, Agent, or Firm* — Tarolli, Sundheim, Covell & Tummino LLP

(57) ABSTRACT

The present invention relates to an intramedullary nail for proximal femoral fractures. The intramedullary nail comprises an elongate body (1) with a longitudinal bore (2). The elongate body (1) includes a proximal portion (5) with an oblique transverse bore (7) for a proximal locking member and a distal portion (6) with at least one transverse bore (8) for a distal locking member. An inlet end of the oblique transverse bore (7) is configured as a recess (9) with a recessed surface (11). The recessed surface (11) is composed of recessed lateral surface portions (15) and a recessed proximal as well as a recessed distal surface portion (16 and 17 respectively). Each of the recessed lateral surface portions (15) is configured with at least one protuberance (18) for preventing or reducing the risk for misalignment of e.g. a reamer and, if misalignment occurs, this will not affect critical parts of the intramedullary nail.

5 Claims, 4 Drawing Sheets

(56) References Cited

U.S. PATENT DOCUMENTS

| | | | |
|---|---|---|---|
| 8,668,695 B2 * | 3/2014 | Schwammberger | A61B 17/7283 606/67 |
| 9,072,552 B2 * | 7/2015 | Simon | A61B 17/7241 |
| 9,358,049 B2 * | 6/2016 | Simon | A61B 17/7241 |
| 2004/0172027 A1 * | 9/2004 | Speitling | A61B 17/744 606/62 |
| 2006/0095039 A1 * | 5/2006 | Mutchler | A61B 17/72 606/64 |
| 2008/0195098 A1 * | 8/2008 | Gotfried | A61B 17/1721 606/62 |
| 2008/0249580 A1 * | 10/2008 | Evans | A61B 17/744 606/86 R |
| 2010/0174284 A1 * | 7/2010 | Schwammberger | A61B 17/7283 606/62 |
| 2010/0179551 A1 * | 7/2010 | Keller | A61B 17/7283 606/67 |
| 2012/0143192 A1 | 6/2012 | Watanabe et al. | |
| 2012/0197255 A1 * | 8/2012 | Elghazaly | A61B 17/725 606/64 |
| 2012/0265202 A1 | 10/2012 | Schwammberger et al. | |
| 2013/0274745 A1 * | 10/2013 | Kmiec, Jr. | A61B 17/72 606/62 |
| 2014/0012259 A1 * | 1/2014 | Matityahu | A61B 17/748 606/62 |
| 2014/0094802 A1 * | 4/2014 | Simon | A61B 17/7241 606/64 |

FOREIGN PATENT DOCUMENTS

| | | |
|---|---|---|
| WO | 2011002903 | 1/2011 |
| WO | 2011044917 | 4/2011 |

* cited by examiner

INTRAMEDULLARY NAIL

RELATED APPLICATION

This application corresponds to PCT/EP2014/075489, filed Nov. 25, 2014, the subject matter, of which is incorporated herein by reference in its entirety.

TECHNICAL FIELD

The present invention relates to an intramedullary nail for proximal femoral fractures. The intramedullary nail comprises an elongate body with a longitudinal bore. The elongate body includes a proximal portion with an oblique transverse bore which extends through said proximal portion for receiving a proximal locking member. The elongate body also includes a distal portion with at least one transverse bore extending through said distal portion for receiving a distal locking member. An inlet end of the oblique proximal transverse bore is configured as a recess with a recessed surface. The recessed surface is composed of recessed lateral surface portions which are directed towards the proximal and distal ends of the intramedullary nail. The recessed surface is further composed of a recessed proximal and a recessed distal surface portion which both are directed towards the sides of the intramedullary nail.

BACKGROUND OF THE INVENTION

Intramedullary nails of the above type are already known in the prior art in many different embodiments. Thus, for repair of trochanteric fractures and fractures of the femoral neck or femoral head, it is known to provide an intramedullary nail which is driven into the femur from the proximal end. The oblique transverse bore in the proximal portion of the elongate body of the nail guides the proximal locking member, e.g. a lag screw, which is introduced into the femoral head via the femoral neck of the femur. As with the lag screw, many proximal locking members are provided with a thread to allow it to be screwed into the femoral head. The proximal portion of the elongate body is configured with the longitudinal bore for, inter alia, insertion therein of a set screw or other coupling or engaging member which interacts with the proximal locking member such that said locking member can move axially in the oblique transverse bore, but not rotate.

Certain of the prior art embodiments have a recessed surface, formed by providing a recess in the intramedullary nail around the inlet end and/or outlet end of the oblique transverse bore in the proximal portion of the nail, to reduce stress and enhance fatigue strength. The recessed surface is defined between outer and inner edges which are formed when the recess is formed, e.g. milled into the outer periphery of the intramedullary nail, and comprises four portions, namely two recessed lateral surface portions which are directed towards the proximal and distal ends of the intramedullary nail, or located to the sides of said nail, and one recessed proximal surface portion as well as one recessed distal surface portion which both are directed towards the sides of the nail or located proximally and distally of the oblique transverse bore. Preferably, the edge constituting the outer limit of the recessed surface can be regarded as forming a rectangle or square with rounded corners.

Nevertheless, if the recessed surface is damaged due to lateral and/or longitudinal misalignment of a reamer or any other hole-generating means when said reamer or said other hole-generating means is used for making a hole for the proximal locking member in the femur, it is damaged in areas with high stress concentration, causing easy damage of the intramedullary nail because the nail will then have about 50% less resistance at and/or close to these damaged areas. Therefore, misalignment of the reamer or said other hole-generating means is critical and constitutes a problem which is not satisfactorily solved in the prior art embodiments.

SUMMARY OF THE INVENTION

It is an object of the present invention to improve an intramedullary nail of the above-mentioned type by configuring the inlet end of the oblique transverse bore in the proximal portion of said nail such that misalignment of a reamer or any other hole-generating means is prevented or at least counteracted, i.e. such that the reamer or said other hole-generating means will be guided into alignment or substantial alignment with said oblique transverse bore in said nail, and damage due to possible misalignment will be reduced because critical parts of the intramedullary nail are not affected.

This is arrived at according to the invention by configuring each of the recessed lateral surface portions of the recessed surface at the inlet end of the oblique transverse bore with at least one protuberance, as defined in claim 1.

Thus, in a primary aspect of the present invention, there is provided an intramedullary nail wherein the protuberance will get in contact with e.g. the reamer first when the reamer is misaligned. Damage due to possible misalignment will then occur in an area where there is less stress. The protuberance is so to say sacrificed to protect the critical area while it at the same time catches the reamer and guides it safely through the intramedullary nail. The resistance to damages of the intramedullary nail as well as the fatigue resistance will be improved.

Preferred embodiments of the intramedullary nail according to the invention and features thereof are defined in the dependent claims.

BRIEF DESCRIPTION OF THE DRAWINGS

The present invention will hereinafter be further explained by means of two non-limiting examples with reference to the accompanying drawings, in which.

It should be noted that the accompanying drawings are not necessarily drawn to scale and that the dimensions of some features of the present invention may have been exaggerated for the sake of clarity.

DETAILED DESCRIPTION OF PREFERRED EMBODIMENTS

The present invention will in the following be exemplified by two embodiments. It should however be realized that the embodiments are included in order to explain the principles of the invention and not to limit the scope of the invention as defined in the appended claims. Details from the embodiments might be combined with each other.

Figure 1:
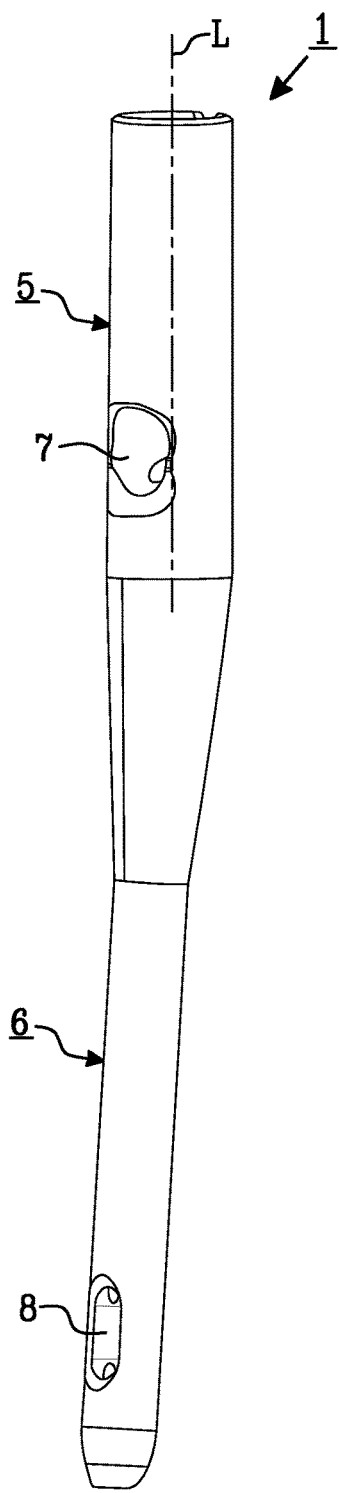
FIG. 1 is a schematic perspective view of a first embodiment of an intramedullary nail according to the present invention.
Figure 2:
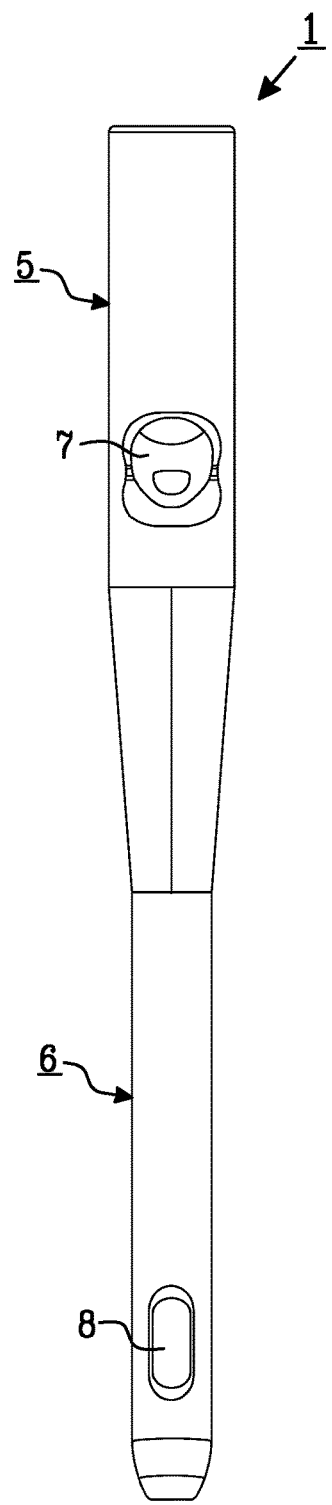
FIG. 2 is a schematic front view of the intramedullary nail according to FIG. 1.
Figure 3:
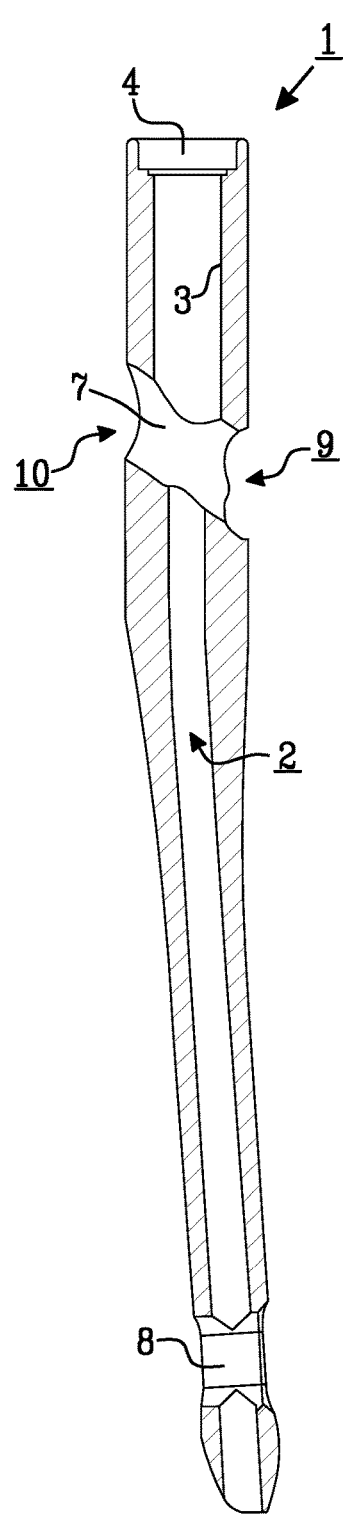
FIG. 3 is a schematic sectional view through the intramedullary nail according to FIGS. 1 and 2.
Figure 6:
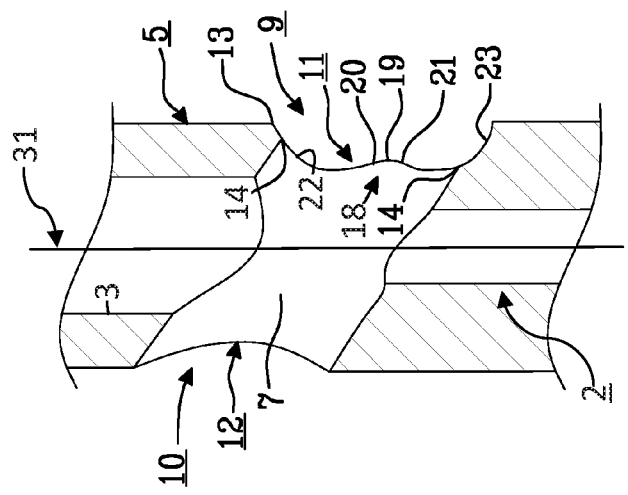
FIG. 6 is a schematic enlarged sectional view of a part of primarily the inlet end of the oblique transverse bore through the proximal portion of the intramedullary nail of FIG. 3.
Figure 5:
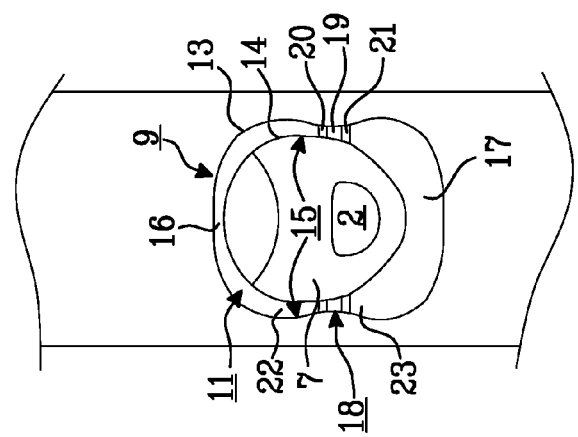
FIG. 5 is a schematic enlarged front view of a part of primarily the inlet end of the oblique transverse bore through the proximal portion of the intramedullary nail of FIG. 2.
Figure 4:
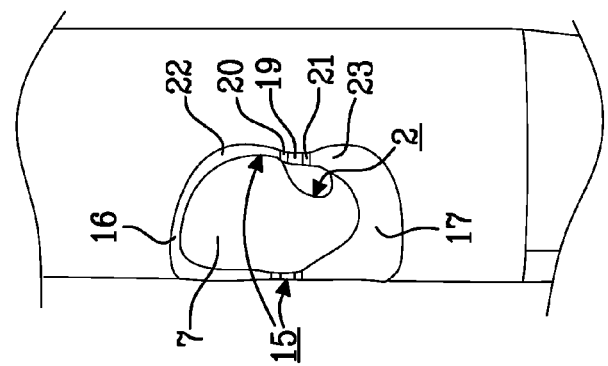
FIG. 4 is a schematic enlarged perspective view of a part of primarily the inlet end of the oblique transverse bore through the proximal portion of the intramedullary nail of FIG. 1.
Figure 7:
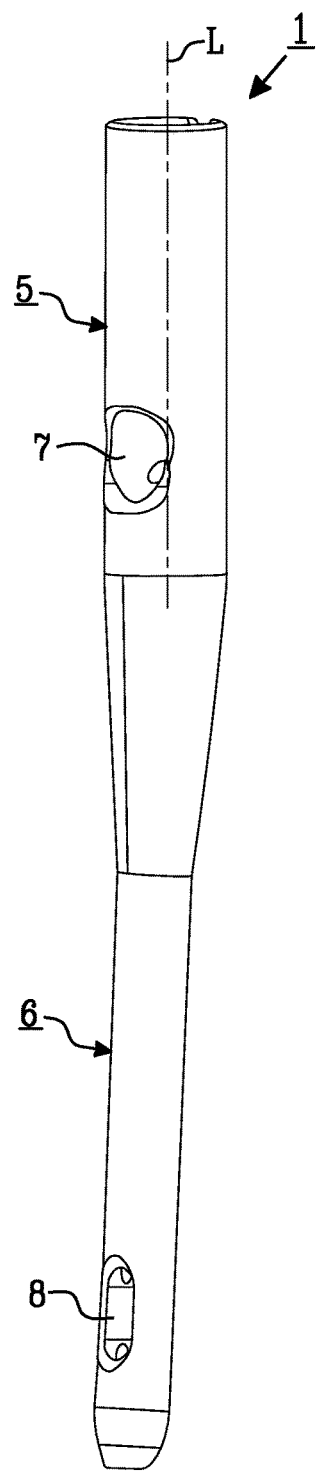
FIG. 7 is a schematic perspective view of a second embodiment of an intramedullary nail according to the present invention.
Figure 8:
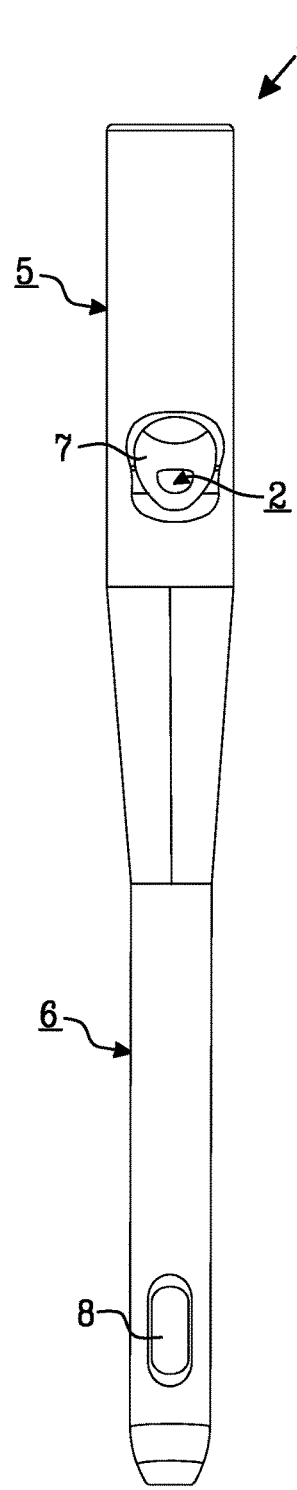
FIG. 8 is a schematic front view of the intramedullary nail according to FIG. 7.
Figure 9:
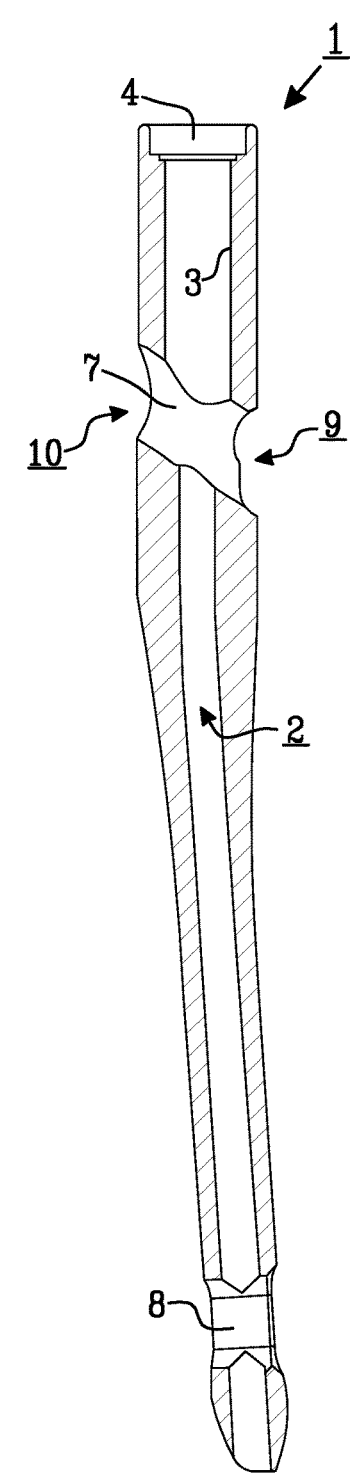
FIG. 9 is a schematic sectional view through the intramedullary nail according to FIGS. 7 and 8.
Figure 12:
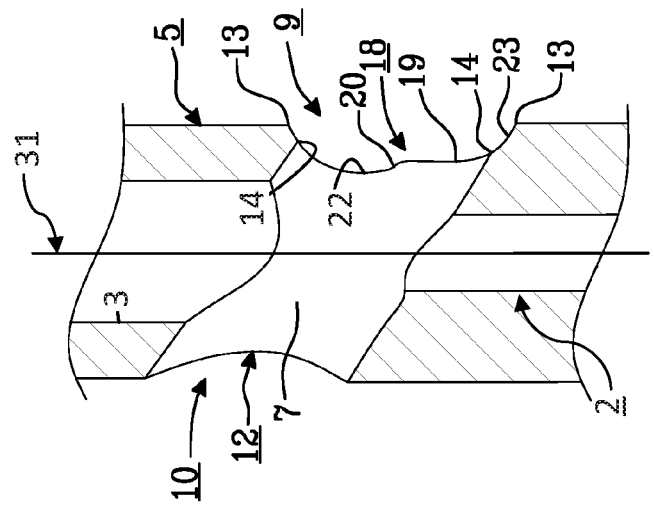
FIG. 12 is a schematic enlarged sectional view of a part of primarily the inlet end of the oblique transverse bore through the proximal portion of the intramedullary nail of FIG. 9.
Figure 11:
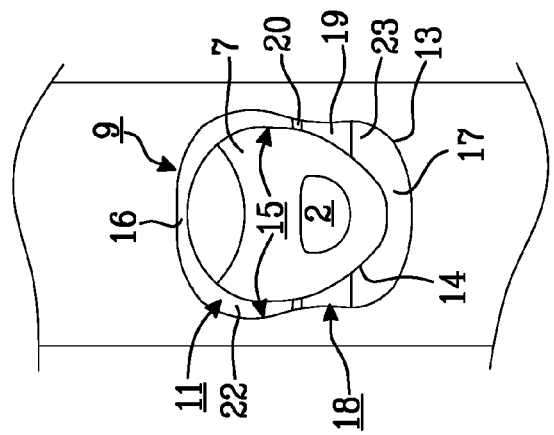
FIG. 11 is a schematic enlarged front view of a part of primarily the inlet end of the oblique transverse bore through the proximal portion of the intramedullary nail of FIG. 8.
Figure 10:
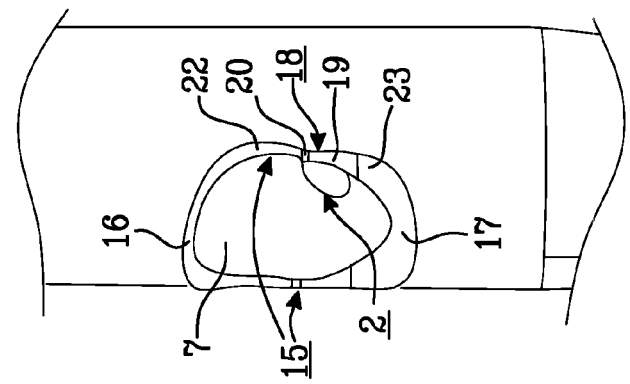
FIG. 10 is a schematic enlarged perspective view of a part of primarily the inlet end of the oblique transverse bore through the proximal portion of the intramedullary nail of FIG. 7.

FIGS. 1 to 3 illustrate as already mentioned a first embodiment of an intramedullary nail according to the present invention and FIGS. 7 to 9 illustrate a second embodiment thereof. The intramedullary nail comprises in both embodiments an elongate body 1 with a longitudinal bore 2. At its proximal end, the longitudinal bore 2 is preferably configured with threads or other means 3 for receiving a set screw or any other suitable coupling or engaging member (not shown). At its proximal end, the longitudinal bore 2 is preferably also configured with threads or a fitting 4 for receiving a suitable mounting and targeting device (not shown) in correct position relative to the intramedullary nail for proper location and fixation of the intramedullary nail in the femur.

The elongate body 1 is made up of a proximal body portion 5 and a distal body portion 6. The proximal body portion 5 is configured with an oblique transverse bore 7. This oblique transverse bore 7 extends through the proximal body portion 5 of the elongate body 1 and is provided for receiving a proximal locking member, preferably a lag screw (not shown) which is screwed into the femoral head. The oblique transverse bore 7 crosses the longitudinal bore 2 such that axial movement of the proximal locking member in the oblique transverse bore, i.e. displacement of the proximal locking member relative to the elongate body 1, is possible, but no rotation, when a set screw or another coupling or engaging member engages the proximal locking member. In order to facilitate rotational locking of the proximal locking member, said member is preferably provided with one or more grooves which extend in the longitudinal direction thereof. The distal body portion 6 is configured with at least one transverse bore 8. This transverse bore 8 extends through the distal body portion 6 of the elongate body 1 and is provided for receiving a distal locking member (not shown) which is screwed into the femoral shaft.

As illustrated in particularly FIGS. 3 and 6 and FIGS. 9 and 12 respectively, the inlet end and the outlet end of the oblique transverse bore 7 are both recessed, i.e. comprises a recess 9 and 10 respectively, in which a recessed surface 11 and 12 respectively, is formed. The recess 9 with the recessed surface 11 at the inlet end pertains to the present invention and will be described in more detail hereinafter, even though the recessed surface 12 at the outlet end may have the same general build-up. As best shown in FIG. 3, 4 and FIG. 7, 8 respectively, the recessed surface 11 is limited by outer and inner edges 13 and 14 respectively, which are formed when the recess 9 is milled or otherwise cut out in the outer periphery of the proximal body portion 5 of the elongate body 1 of the intramedullary nail. Thus, between said outer and inner edges 13, 14 of the recessed surface 11, there are provided two recessed lateral surface portions 15 which are directed towards the proximal and distal ends of the elongate body 1 of the intramedullary nail, or located to the sides of said body or nail, and one recessed proximal and one recessed distal surface portion 16 and 17 respectively, which both are directed towards the sides of the body or nail or located proximally and distally of the oblique transverse bore 7 at the inlet end thereof. Accordingly, the edge 13 constituting the outer limit of the recessed surface portions 15, 16, 17 of the recessed surface 11 has four sides, forming, generally seen, a rectangle or square with rounded corners. For obvious reasons, the outer edge 13 of the recessed surface 11 is found in the outer periphery of the proximal body portion 5 of the body 1 or nail. The inner edge 14 of the recessed surface 11 is formed by the oblique transverse bore 7. The recessed surface portions 15, 16, 17 thereby forming an endless recessed surface 11, may be partly chamfered. The distance between the outer and inner edges 13, 14 of the recessed surface 11 may thereby vary, as is particularly shown at the recessed distal surface portion 17.

According to the present invention, each of the recessed lateral surface portions 15 of the recessed surface 11 at the inlet end of the oblique transverse bore 7 are configured with at least one protuberance 18. The object of the protuberances 18 is as stated above to prevent or at least counteract misalignment of a hole-generating means, e.g. a reamer, by guiding said hole-generating means, e.g. said reamer, into correct alignment or substantially correct alignment with the oblique transverse bore 7, and, if misalignment nevertheless occurs to any extent, reduce damage of critical parts of the intramedullary nail by using the protuberances to take up the stresses incurred on the nail due to said misalignment. In the illustrated embodiments, one protuberance 18 is formed on each recessed lateral surface portion 15. The protuberances 18 are formed preferably at the same time the recess 9 with the recessed surface 11 is milled or in any other way cut out of the outer periphery of the proximal body portion 5 of the elongate body 1 of the intramedullary nail.

Each protuberance 18 is at least partly configured to run substantially in parallel with a longitudinal axis L of the proximal body portion 5 of the elongate body 1.

The size and shape of each protuberance 18 may vary. FIGS. 1 to 6 and FIGS. 7 to 12 illustrate two different embodiments of the protuberances 18.

Thus, in FIGS. 1 to 6 an intramedullary nail is illustrated, wherein the protuberance 18 on each recessed lateral surface portion 15 is proximally and distally of the parallel part 19 thereof configured to run at an angle towards a longitudinal plane 31 extending transverse to the oblique bore 7 through the proximal body portion 5 of the elongate body 1 of the nail. As illustrated, the protuberance 18 on each recessed lateral surface portion 15 is proximally and distally of the parallel part 19 thereof configured to run in the form of an arc towards the longitudinal plane 31 extending transverse to the oblique bore 7 through the proximal body portion 5 of the elongate body 1, i.e. the proximal and distal parts 20 and 21 respectively, of the protuberance are curved and preferably continuously curved towards said longitudinal plane 31. Alternatively, the proximal and distal parts 20, 21 of the protuberance 18 may be straight or partly straight and partly curved.

The recess 9 at the inlet end of the oblique transverse bore 7 has a maximum height of about 10 to 20 mm, preferably about 14.5 mm, i.e. the maximum distance between the outer edge 13 at the recessed proximal surface portion 16 and the outer edge 13 at the recessed distal surface portion 17 measured in the longitudinal direction of the proximal body portion 5 of the elongate body 1 of the intramedullary nail, is in the embodiment of FIGS. 1 to 6 about 10 to 20 mm, preferably about 14.5 mm. However, the maximum height of the recess 9 at the inlet end of the oblique transverse bore 7 may lie outside the above-mentioned interval.

In FIGS. 7 to 12, the protuberance 18 on each recessed lateral surface portion 15 is proximally of the parallel part 19 thereof configured to run at an angle towards a longitudinal plane 31 extending transverse to the oblique bore 7 through the proximal body portion 5 of the elongate body 1 of the nail, and distally of said parallel part thereof configured to directly pass over into a distal part of the recessed lateral surface portion 15, i.e. there is no distal part of the protuberance 18 in the embodiment of FIGS. 7 to 12 which correspond to the distal part 21 of the protuberance 18 in the embodiment of FIGS. 1 to 6. Accordingly, compared to the embodiment of FIGS. 1 to 6, the protuberance 18 on each recessed lateral surface portion 15 is here only proximally of the parallel part 19 thereof configured to run in the form of an arc towards the longitudinal plane 31 extending transverse to the oblique bore 7 through the proximal body portion 5 of the elongate body 1, i.e. only the proximal part 20 of the protuberance is curved and preferably continuously curved towards said longitudinal plane 31. Alternatively, the proximal part 20 of the protuberance 18 may be straight or partly straight and partly curved.

The recess 9 at the inlet end of the oblique transverse bore 7 has a maximum height of about 10 to 20 mm, preferably about 15 mm, i.e. the maximum distance between the outer edge 13 at the recessed proximal surface portion 16 and the outer edge 13 at the recessed distal surface portion 17 measured in the longitudinal direction of the proximal body portion 5 of the elongate body 1 of the intramedullary nail, is in the embodiment of FIGS. 7 to 12 about 10 to 20 mm, preferably about 15 mm. However, the maximum height of the recess 9 at the inlet end of the oblique transverse bore 7 may lie outside the above-mentioned interval.

By means of the above-mentioned particular configuration of the protuberances 18, correction of possible misalignment, lateral and/or longitudinal, of e.g. a reamer relative to the oblique transverse bore 7 and correct guiding of said reamer into said bore is facilitated. Also, the big difference between the two embodiments described above is that the protuberances 18 illustrated in FIGS. 7 to 12 have a longer parallel part 19 than the protuberances of FIGS. 1 to 6 and that said former protuberances directly pass over into the part of the recessed lateral surface portion located distally of said protuberances. In use, this longer parallel part 19 thereby further improves guiding of the reamer or any other hole-generating means into the oblique transverse bore 7 at the upper, proximal part of the recess 9. It is possible within the scope of the invention to further modify the protuberances 18 such that they can guide a reamer or any other hole-generating means upwards into the oblique transverse bore 7 at the upper part of the inlet-end recess 9 in the proximal portion 5 of the elongate body 1 which constitutes the intramedullary nail, and take up any stresses to which the intramedullary nail is subjected because of misalignment of the reamer or said other hole-generating means.

As can be seen particularly in FIG. 2, 5 and FIG. 8, 11 respectively, the protuberances 18 give the outer edge 13 of the recessed surface 11 and accordingly also the recessed surface itself, the form of having a "slender waist" when seen from the front, i.e. the recessed lateral surface portions 15 are not completely straight or flattened nor are they rounded in their general appearance, but form rather a restriction of the width of the recess 9 at the protuberances. This feature is less outstanding in the embodiment of FIGS. 7 to 12, because the length of the recessed proximal surface portion 16 is larger than the length of the recessed distal surface portion 17.

Another feature contributing to the particular design of the recessed surface 11 and of the recess 9 when seen from the side is, except of course for the protuberance 18, that each recessed lateral surface portion 15 is proximally and distally of the protuberance 18 configured to run in the form of an arc away from the longitudinal plane extending transverse to the oblique bore 7 through the proximal portion 5 of the elongate body 1 of the intramedullary nail. These proximal and distal parts of each recessed lateral surface portion 15 are denominated 22 and 23 respectively. The radius of the arcuate proximal part 22 of each recessed lateral surface portion 15 is about 5 to 15 mm, preferably about 10 mm and the radius of the arcuate distal part 23 is about 4 to 12 mm, preferably about 8 mm. It should be noted however, that the radius of the arcuate proximal part 22 as well as the radius of the arcuate distal part 23 of each recessed lateral surface portion 15 may lie outside the above-mentioned interval.

Further modifications of the present invention within the scope of the appended claims are feasible without departing from the idea and object of the invention. As such, the present invention should not be considered as limited by the embodiments described above or by the figures illustrating these embodiments. Rather, the full scope of the invention should be determined by the appended claims with reference to the description and drawings. Thus, although the protuberances are illustrated as being integral with the recessed lateral surface portions, it should be possible to alternatively provide the protuberances e.g. as separate members and attach them in a suitable way and where appropriate to said recessed lateral surface portions. It will then also be possible to manufacture the protuberances in a suitable material with optimum capacity to resist forces generated by misaligned reamers or other hole-generating means and with optimum capacity for guiding or re-directing misaligned reamers or other hole-generating means, and to thereby also manufacture the protuberances such that they will get the best possible shape for their guiding purposes. Attachment of the protuberances for configuring the recessed lateral surface portions therewith can be performed such that the attachment is permanent or releasable.

The invention claimed is:
1. An intramedullary nail for proximal femoral fractures, comprising:
   an elongate body (1) with a longitudinal bore (2),
   wherein said elongate body (1) includes a proximal portion (5) with an oblique transverse bore (7) extending through said proximal portion for receiving a proximal locking member, and a distal portion (6) with at least one transverse bore (8) extending through said distal portion for receiving a distal locking member, and wherein an inlet end of the proximal transverse bore (7) is configured as a recess (9) with a recessed surface (11), said recessed surface being composed of recessed lateral surface portions (15), a recessed proximal surface portion (16) and a recessed distal surface portion (17), the recessed surface (11) being limited by outer and inner edges (13,14) formed when the recess (9) is cut out in the outer periphery of the proximal body portion (5) of the elongate body, the recessed lateral surface portions (15) being provided between the inner and outer edges (13,14) and are each configured with at least one protuberance (18), each protuberance (18) having a parallel part extending toward the recessed proximal surface portion and the recessed distal surface portion, the parallel part of each protuberance being parallel with a longitudinal axis (L) of the proximal body portion (5) of the elongate body (1), and a part of each protuberance (18) that is proximal the parallel part (19) running at an angle towards a longitudinal plane extending transverse to the oblique bore (7) through the proximal body portion (5) of the elongate body (1), and a part of each protuberance that is distal the parallel part running parallel to the longitudinal plane and into a distal part (23) of the recessed lateral surface portion (15), whereby each protuberance (18) is configured to guide a hole-generating means into alignment with the oblique transverse bore (7) and to reduce damage to the intramedullary nail due to misalignment.

2. The intramedullary nail according to claim 1, wherein the part of each protuberance (18) that is proximal the parallel part (19) runs in the form of an arc towards the longitudinal plane extending transverse to the oblique bore (7) through the proximal body portion (5) of the elongate body (1).

3. The intramedullary nail according to claim 1, wherein the maximum length of the recess (9) is 10 to 20 mm.

4. The intramedullary nail according to claim 3, wherein the maximum length of the recess (9) is about 15 mm.

5. The intramedullary nail according to claim 1, wherein the length of the recessed proximal surface portion (16) is larger than the length of the recessed distal surface portion (17).

* * * * *